US00PP36126P2

(12) United States Plant Patent
Kobayashi

(10) Patent No.: US PP36,126 P2
(45) Date of Patent: Sep. 17, 2024

(54) NEW GUINEA IMPATIENS PLANT NAMED 'Dongirolcoa'

(50) Latin Name: *Impatiens hawkeri*
Varietal Denomination: Dongirolcoa

(71) Applicant: DUMMEN GROUP B.V., De Lier (NL)

(72) Inventor: Ruth Kobayashi, Carlsbad, CA (US)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/526,967

(22) Filed: Dec. 1, 2023

(51) Int. Cl.
*A01H 5/02* (2018.01)
*A01H 6/16* (2018.01)

(52) U.S. Cl.
USPC ..... Plt./318.7

(58) Field of Classification Search
USPC ..... Plt./263.1, 317, 318.7
See application file for complete search history.

*Primary Examiner* — Karen M Redden
(74) *Attorney, Agent, or Firm* — C. Anne Whealy

(57) ABSTRACT

A new and distinct cultivar of *Impatiens* plant named 'Dongirolcoa' characterized by its relatively compact, upright to outwardly spreading and mounding plant habit; moderately vigorous growth habit; freely branching habit; dense and full appearance; dark green-colored leaves; freely and early flowering habit; medium to large-sized ruffled intense purplish red-colored flowers; and good garden performance.

2 Drawing Sheets

Figure 1:
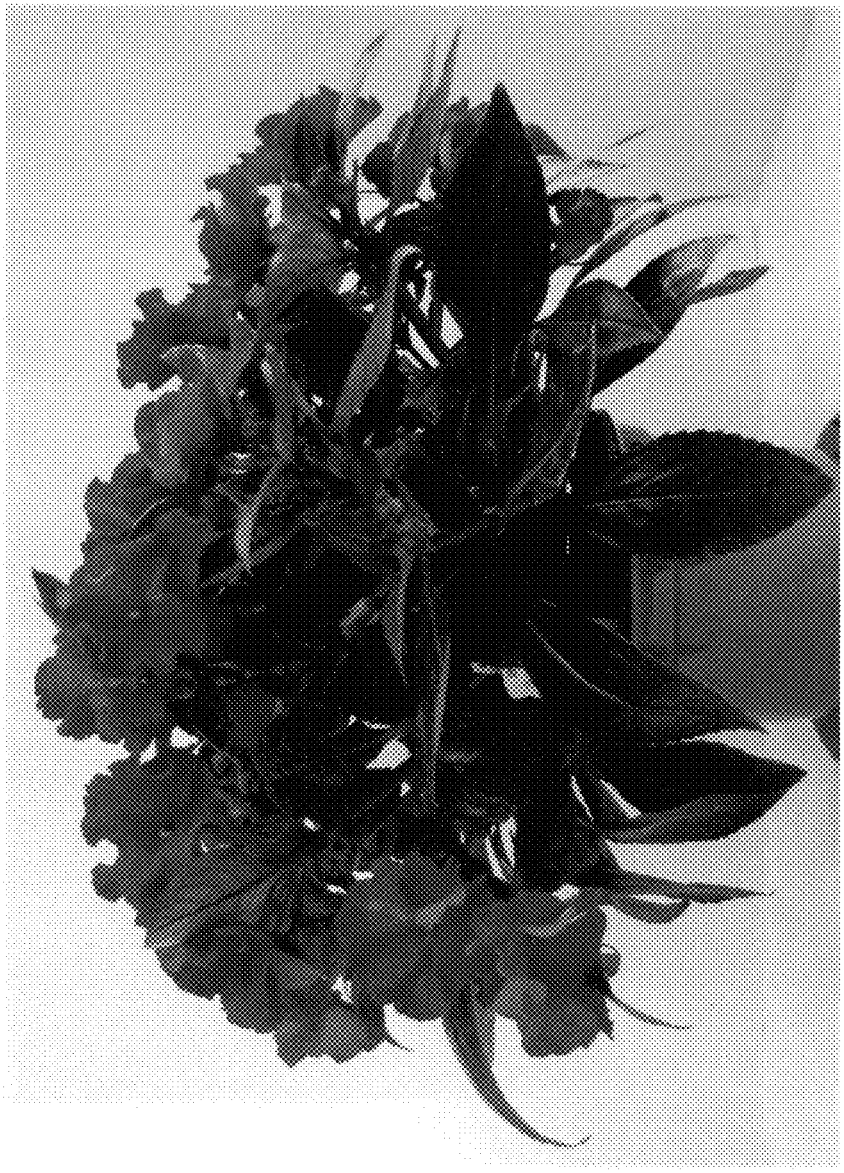

Botanical designation: *Impatiens hawkeri.*
Cultivar denomination: 'DONGIROLCOA'.

STATEMENT REGARDING PRIOR DISCLOSURES BY INVENTOR & APPLICANT/ASSIGNEE

The Inventor and Applicant/Assignee assert that no sales, offers for sale or public distribution of the instant plant occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of New Guinea *Impatiens* plant, botanically known as *Impatiens hawkeri* and hereinafter referred to by the name 'Dongirolcoa'.

The new *Impatiens* plant is a product of a planned breeding program conducted by the Inventor in Koka, Ethiopia and Encinitas, California. The objective of the breeding program is to create new freely-branching, early and freely flowering New Guinea *Impatiens* plants with large attractive flowers and good garden performance.

The new *Impatiens* plant originated from a cross-pollination made by the Inventor in November, 2019 in Koka, Ethiopia of a proprietary selection of *Impatiens hawkeri* identified as code number NN17-646548-005, not patented, as the female, or seed, parent with *Impatiens hawkeri* 'Dongirolre', disclosed in U.S. Plant Pat. No. 34,029, as the male, or pollen, parent. The new *Impatiens* plant was discovered and selected by the Inventor as a single flowering plant from within the progeny of the stated cross-pollination in a controlled greenhouse environment in Encinitas, California in April, 2020.

Asexual reproduction of the new *Impatiens* plant by terminal vegetative cuttings in a controlled greenhouse environment in Encinitas, California since June, 2020 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongirolcoa'. These characteristics in combination distinguish 'Dongirolcoa' as a new and distinct *Impatiens* plant:

1. Relatively compact, upright to outwardly spreading and mounding plant habit.
2. Moderately vigorous growth habit.
3. Freely branching habit; dense and full appearance.
4. Dark green-colored leaves.
5. Freely and early flowering habit.
6. Medium to large-sized ruffled intense purplish red-colored flowers.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are more vigorous than and not as compact as plants of the female parent selection.
2. Plants of the new *Impatiens* have larger flowers than plants of the female parent selection.
3. Flowers of plants of the new *Impatiens* are more ruffled and undulating than flowers of plants of the female parent selection.
4. Flowers of plants of the new *Impatiens* are intense purplish red in color whereas flowers of plants of the female parent selection are medium red in color.

Plants of the new *Impatiens* can be compared to plants of the male parent, 'Dongirolre'. Plants of the new *Impatiens* differ primarily from plants of 'Dongirolre' in flower color as flowers of plants of the new *Impatiens* are intense purplish red in color whereas flowers of plants of 'Dongirolre' are vivid red in color.

Plants of the new *Impatiens* can be compared to plants of *Impatiens hawkeri* 'Kironanete', disclosed in U.S. Plant Pat. No. 26,753. In side-by-side comparisons, plants of the new *Impatiens* differ primarily from plants of 'Kironanete' in the following characteristics:

1. Plants of the new *Impatiens* are more vigorous than plants of 'Kironanete'.
2. Flowers of plants of the new *Impatiens* are intense purplish red in color whereas flowers of plants of 'Kironanete' are dark cherry red in color.

Plants of the new *Impatiens* can also be compared to plants of *Impatiens hawkeri* 'Dongimprolhopin', disclosed in U.S. Plant Pat. No. 32,148. In side-by-side comparisons, plants of the new *Impatiens* differ primarily from plants of 'Dongimprolhopin' in the following characteristics:

1. Plants of the new *Impatiens* are more vigorous than and not as compact as plants of 'Dongimprolhopin'.
2. Plants of the new *Impatiens* have smaller flowers than plants of 'Dongimprolhopin'.
3. Flowers of plants of the new *Impatiens* are intense purplish red in color whereas flowers of plants of 'Dongimprolhopin' are bright red purple in color.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (FIG. 1) is a side perspective view of a typical flowering plant of 'Dongirolcoa' grown in a container.

Figure 2:
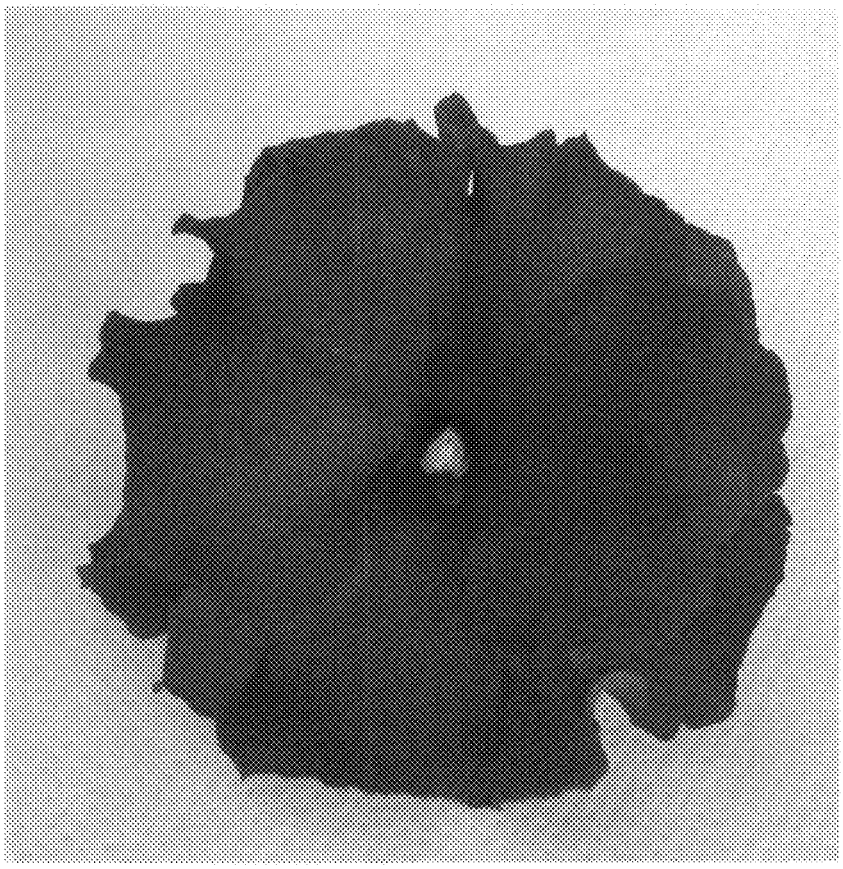

The photograph on the second sheet (FIG. 2) is a close-up view of a typical flower of 'Dongirolcoa'.

DETAILED BOTANICAL DESCRIPTION

The aforementioned photographs and following observations, measurements and values describe plants grown during the summer in 16.5-cm containers in a polyethylene-covered greenhouse in Encinitas, California and under cultural practices typical of commercial New Guinea *Impatiens* production. During the production of the plants, day temperatures averaged 25 C, night temperatures averaged 18 C and light levels ranged from 4,000 to 4,500 lux. Plants were 16 weeks old when the photographs were taken and 17 weeks old when the description was taken. In the following description, color references are made to The Royal Horticultural Society Colour Chart, 2015 Edition, except where general terms of ordinary dictionary significance are used.

Botanical classification: *Impatiens hawkeri* 'Dongirolcoa'.

Parentage:

*Female, or seed, parent.*—Proprietary selection of *Impatiens hawkeri* identified as code number NN17-646548-005, not patented.

*Male, or pollen, parent.*—*Impatiens hawkeri* 'Dongirolre', disclosed in U.S. Plant Pat. No. 34,029.

Propagation:

*Type.*—By terminal vegetative cuttings.

*Time to initiate roots, summer and winter.*—About five to seven days at temperatures about 27 C and night temperatures about 20 C.

*Time to produce a rooted young plant, summer and winter.*—About three weeks at day temperatures about 27 C and night temperatures about 20 C.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Relatively compact, upright to outwardly spreading and mounding plant habit; broad inverted triangle in overall shape; freely branching habit with lateral branches potentially developing at every node; dense and full appearance; moderately vigorous growth habit and moderate growth rate.

*Plant height.*—About 26.5 cm.

*Plant diameter.*—About 45.5 cm.

Lateral branch description:

*Length.*—About 21 cm.

*Diameter.*—About 1.3 cm.

*Internode length.*—About 4.75 cm to 6.5 cm.

*Strength.*—Strong, stout; flexible.

*Aspect.*—Initially upright to outwardly spreading.

*Texture and luster.*—Smooth, glabrous; glossy.

*Color, developing and fully developed.*—Close to 148A variably overlain with close to 185A and 187A.

Leaf description:

*Arrangement.*—Typically in whorls; simple.

*Length.*—About 7 cm to 7.5 cm.

*Width.*—About 3 cm to 3.5 cm.

*Shape.*—Elliptic to narrowly ovate.

*Apex.*—Acuminate.

*Base.*—Attenuate to cuneate.

*Margin.*—Serrate with ciliation.

*Texture and luster, upper and lower surfaces.*—Smooth, glabrous; semi-glossy.

*Venation pattern.*—Pinnate; arcuate.

*Color.*—Developing leaves, upper surface: Initially, darker green than 146A becoming closer to NN137A. Developing leaves, lower surface: Initially, close to 146A to 146B becoming closer to 147B. Fully expanded leaves, upper surface: Close to NN137A; venation, proximally, close to 59B and distally, close to 144A. Fully expanded leaves, lower surface: Close to 147B; venation, close to 183A and 183B.

*Petiole length.*—About 2 cm to 2.2 cm.

*Petiole diameter.*—About 2.75 mm to 3 mm.

*Petiole texture and luster, upper and lower surfaces*.—Smooth, glabrous; moderately glossy.

*Petiole color, upper surface*.—Close to 183A to 183B.

*Petiole color, lower surface*.—Close to 187C.

Flower description:

*Flower type and flowering habit*.—Single, large ruffled rounded rectangular axillary flowers; freely flowering habit, typically about four to six open flowers and flower buds per lateral branch; flowers positioned above and beyond the foliar plane, flowers typically face mostly upright to outwardly.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about eleven weeks after planting.

*Flower buds, before showing petal color*.—Length: About 1 cm. Diameter: About 6 mm. Shape: Ovoid; rosebud-like when opening. Texture and luster: Smooth, glabrous; moderately glossy. Color: Close to 144A to 144B variably overlain with close to 185A and 185B.

*Flower diameter*.—About 6.75 cm by 7 cm.

*Flower depth*.—About 2.5 cm to 2.75 cm.

*Petals*.—Quantity and arrangement: Five per flower in a single whorl. Length, banner petal: About 3.6 cm. Length, lateral petals: About 3.25 cm. Length, lower petals: About 3.3 cm. Width, banner petal: About 5.4 cm. Width, lateral petals: About 4.6 cm. Width, lower petals: About 4.6 cm. Shape, all petals: Broadly spatulate. Apex, all petals: Emarginate with irregular praemorse tendencies. Base, all petals: Attenuate. Margin, all petals: Mostly entire with occasional and random indentations; undulate, ruffled and frilled appearance. Texture and luster, all petals, upper surface: Smooth, glabrous; velvety; slightly glossy; iridescent. Texture and luster, all petals, lower surface: Smooth, glabrous; slightly glossy; iridescent. Color, all petals: When opening, upper surface: More intense than N57A. When opening, lower surface: Close to N66B. Fully opened, upper surface: More intense than N57A and at the throat, close to 53A; venation, similar to lamina colors; color does not change with subsequent development. Fully opened, lower surface: Close to N66B to N66C; venation, close to N66B to N66C; color does not change with subsequent development.

*Sepals*.—Quantity and arrangement: Three in a single whorl; one modified into an elongated spur. Lateral sepals length: About 8 mm. Lateral sepals width: About 6.5 mm. Spur sepal length: About 1 cm. Spur sepal width: About 1.2 cm. Lateral sepals shape: Ovate. Spur sepal shape: Broadly ovate. Sepal apex, all sepals: Acuminate to cuspidate. Sepal base, all sepals: Truncate. Sepal margin, all sepals: Entire. Sepal texture and luster, all sepals, upper and lower surfaces: Smooth, glabrous; semi-glossy. Lateral sepals color, upper surface: Close to 144A to 144B. Lateral sepals color, lower surface: Close to 144A to 144B variably tinged with close to 53A. Spur sepal color, upper surface: Close to N66A to N66B. Spur sepal color, lower surface: Close to N66C. Spur length: About 3.5 cm. Spur diameter: At flower, about 3 mm; at apex, less than 1 mm. Spur texture and luster: Smooth, glabrous; semi-glossy. Spur color: Close to 60A.

*Peduncles*.—Length: About 3 cm to 3.5 cm. Diameter: About 2 mm to 2.25 mm. Angle: About 45 degrees from stem axis. Strength: Strong; flexible. Texture and luster: Smooth, glabrous; moderately glossy. Color: Close to 60A.

*Reproductive organs*.—Stamens: Quantity: Five fused at anthers; filaments free. Anther size: About 1 mm by 2.5 mm. Anther shape: Oblong. Anther color: Close to 10D. Pollen amount: Scarce to moderate. Pollen color: Close to 158A. Pistils: Quantity per flower: One. Pistil length: About 4.5 mm. Stigma shape: Crested. Stigma color: Close to 144A. Style color: Close to 144A. Ovary color: Close to 144A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5 C to about 40 C.

It is claimed:

1. A new and distinct *Impatiens* plant named 'Dongirolcoa' as illustrated and described.

* * * * *